United States Patent
Allen et al.

(10) Patent No.: US 6,490,148 B1
(45) Date of Patent: Dec. 3, 2002

(54) INSTALLATION OF FILTER CAPACITORS INTO FEEDTHROUGHS FOR IMPLANTABLE MEDICAL DEVICES

(75) Inventors: Kevin M. Allen, Eldersburg, MD (US); Thomas W. Shipman, Columbia, MD (US); Allan S. Gelb, Orlando, FL (US)

(73) Assignee: Greatbatch-Hittman, Incorporated, Columbia, MD (US)

( * ) Notice: Subject to any disclaimer, the term of this patent is extended or adjusted under 35 U.S.C. 154(b) by 0 days.

(21) Appl. No.: 10/037,840

(22) Filed: Jan. 2, 2002

(51) Int. Cl.[7] .............................................. H01G 4/228
(52) U.S. Cl. ..................................... 361/302; 361/306.1
(58) Field of Search .............................. 361/302, 306.1, 361/321.2; 174/152 GM, 50.61; 607/36, 37, 9

(56) References Cited

U.S. PATENT DOCUMENTS

| | | |
|---|---|---|
| 3,600,787 A | 8/1971 | Lindsay |
| 4,446,502 A | 5/1984 | Boser et al. |
| 4,678,868 A | 7/1987 | Kraska et al. |
| 5,050,034 A | 9/1991 | Hegner et al. |
| 5,406,444 A | 4/1995 | Selfried et al. |
| 5,531,003 A | 7/1996 | Seifried et al. |
| 5,870,272 A | 2/1999 | Seifried et al. |
| 5,905,627 A | 5/1999 | Brendel et al. |
| 6,008,980 A | 12/1999 | Stevenson et al. |
| 6,031,710 A | 2/2000 | Wolf et al. |
| 5,055,455 A | 4/2000 | O'Phelan et al. |
| 6,275,369 B1 * | 8/2001 | Stevenson et al. .......... 361/302 |

* cited by examiner

Primary Examiner—Anthony Dinkins
(74) Attorney, Agent, or Firm—Hodgson Russ LLP (57) ABSTRACT

A feedthrough device and brazing process for joining the constituent parts of the feedthrough device, while allowing a lead to pass therethrough in a nonconductive manner. The feedthrough comprises at least one lead, a ferrule defining a capacitor recess and defining an insulator recess, an insulator disposed in the insulator recess of the ferrule, the insulator defining a passageway sized to allow the lead to pass therethrough. The feedthrough further comprises a capacitor disposed in the capacitor recess and defining a capacitor passageway sized to allow the lead to pass threrethrough, and the capacitor comprises first and second sets of plates, wherein the first set of plates is conductively coupled to the ferrule and the second set of plates is conductively coupled to the lead. Brazing is a two step process wherein the braze joints between the insulator and the lead and between the insulator and ferrule are formed first at a first temperature using an insulator braze material. The second step of brazing is performed at a lower temperature than the brazing in the first step, and utilizes capacitor braze materials that are different from the insulator braze materials in that they have lower melting temperatures than the insulator braze materials.

20 Claims, 4 Drawing Sheets

INSTALLATION OF FILTER CAPACITORS INTO FEEDTHROUGHS FOR IMPLANTABLE MEDICAL DEVICES

BACKGROUND

This invention relates to feedthroughs for providing an electrical path for implantable medical devices including electrical pulse generators. Examples of such devices are implantable cardiac pacemakers and implantable cardiac defibrillators for correction of cardiac abnormalities. The pacemaker or defibrillator device has a housing containing a pulse generator including associated circuitry and a battery that serves as a power supply. A conductive lead or pin extends from the pulse generator circuit in the interior of the device and passes through the device housing where it is connected via a medical lead to an electrode surgically attached to an appropriate location in the heart.

One of the concerns related to the use of such implantable medical devices (pacemakers, defibrillators, etc.) is that they are subject to stray electromagnetic interference (EMI). Such EMI may come from sources such as television transmitters, cell phones, theft detection devices and so on. This spurious EMI is highly undesirable because it can interfere with proper functioning of the implanted medical device, either by inhibiting a proper response or by causing an improper one. Such stray EMI can essentially be eliminated as a problem source by shunting the EMI to ground with the use of a filter capacitor connected between the input lead wire(s) and electrical ground. Typically, one capacitor is positioned between each such lead wire and ground. These capacitors are often built into a monolithic structure or array when used for a multilead feedthrough. If the array is in the form of a right circular cylinder, it is designated a discoidal capacitor.

However, these prior art type feedthroughs routinely use conductive polymeric materials such as polyimides and epoxies or metallic materials such as solder alloys for holding their constituent parts together. Use of the conductive polymeric materials requires care in preventing leakage of the conductive polymer into locations in the assembly where it could cause a short circuit rendering the implantable medical device inoperative. In addition, conductive polymers exhibit relatively low electrical conductivity as compared with metallic materials. The bonding mechanism between the conductive polymer and the metallic members of the feedthrough is predominately mechanical, resulting in a relatively weak electrical and mechanical connection. Solders have relatively low melting temperatures such that subsequent high temperature welding operations on other parts of the device can compromise the soldered joint or cause beading in which a ball or pellet of solder could fall into a location in the device where a short circuit could result. Additionally, some soldering operations require the use of fluxes that leave behind undesirable residues after the soldering is completed, that can be a source of entrapped moisture, possibly resulting in device failure. Thus, there is a need for a better filtered feedthrough device as well as a better filtered feedthrough assembly process.

SUMMARY

The present invention provides a feedthrough assembly and a method of making the same wherein capacitive arrays are installed into a single or multi-pin feedthroughs using a brazing process. The braze material serves to join the capacitor to the feedthrough, holding it securely in place. In addition, the braze material provides the electrical connection from one set(s) of internal capacitor plates to the flange or ferrule and from the opposing set(s) of plates to the feedthrough lead wire(s).

In particular, the feedthrough comprises a lead or conductive pin, a ferrule defining a capacitor receiving recess and an insulator receiving recess, a capacitor disposed in the capacitor receiving recess and defining a capacitor passageway for the lead to pass therethrough, and an insulator disposed in the insulator receiving recess and defining an insulator passageway for the lead to pass through. The lead or pin passes through the insulator in a nonconductive manner. The capacitor comprises first and second sets of plates separated by a dielectric, the first set of plates being conductively coupled to the ferrule and the second set of plates being conductively coupled to the lead so that the lead or pin passes through the ferrule in a non-contacting and nonconductive manner. An insulator braze material is used for forming the insulator-lead braze joint and the insulator-ferrule braze joint. A capacitor braze material is used for forming the capacitor-ferrule braze joint and the capacitor-lead braze joint.

The insulator braze material is typically gold, while the capacitor braze material is a composition selected to be compatible with the termination materials used in the capacitor. The brazing process is a two step procedure wherein the first step calls for the brazing of the insulator-lead braze joint and the insulator-ferrule braze joint at a first temperature using a selected insulator braze material. The second step of brazing calls for brazing the capacitor-ferrule braze joint and the capacitor-lead braze joint, with the selected capacitor braze material at a second temperature that is lower than the first temperature. The braze materials for each step described in the detailed description. This second brazing process does not damage, weaken, or otherwise destroy the insulator-ferrule braze joint or insulator-lead braze joint formed in the previous operation (first step of the brazing process) because if is performed at a lower temperature.

A durable feedthrough assembly is thus provided that is superior to the prior art because the feedthrough can withstand subsequent welding processes without losing its integrity and because the constituent parts of the feedthrough are brazed together. If a solder were used, it might melt, weaken, and bead up at the increased temperatures encountered during welding and a compromised joint could thus result. Furthermore, beads of solder could form if soldering were employed and they could fall into the region of the implantable device containing the electrical components causing short circuits and other problems. The present invention avoids these problems and thus successfully overcomes problems associated with the prior art.

DETAILED DESCRIPTION

Figure 1:
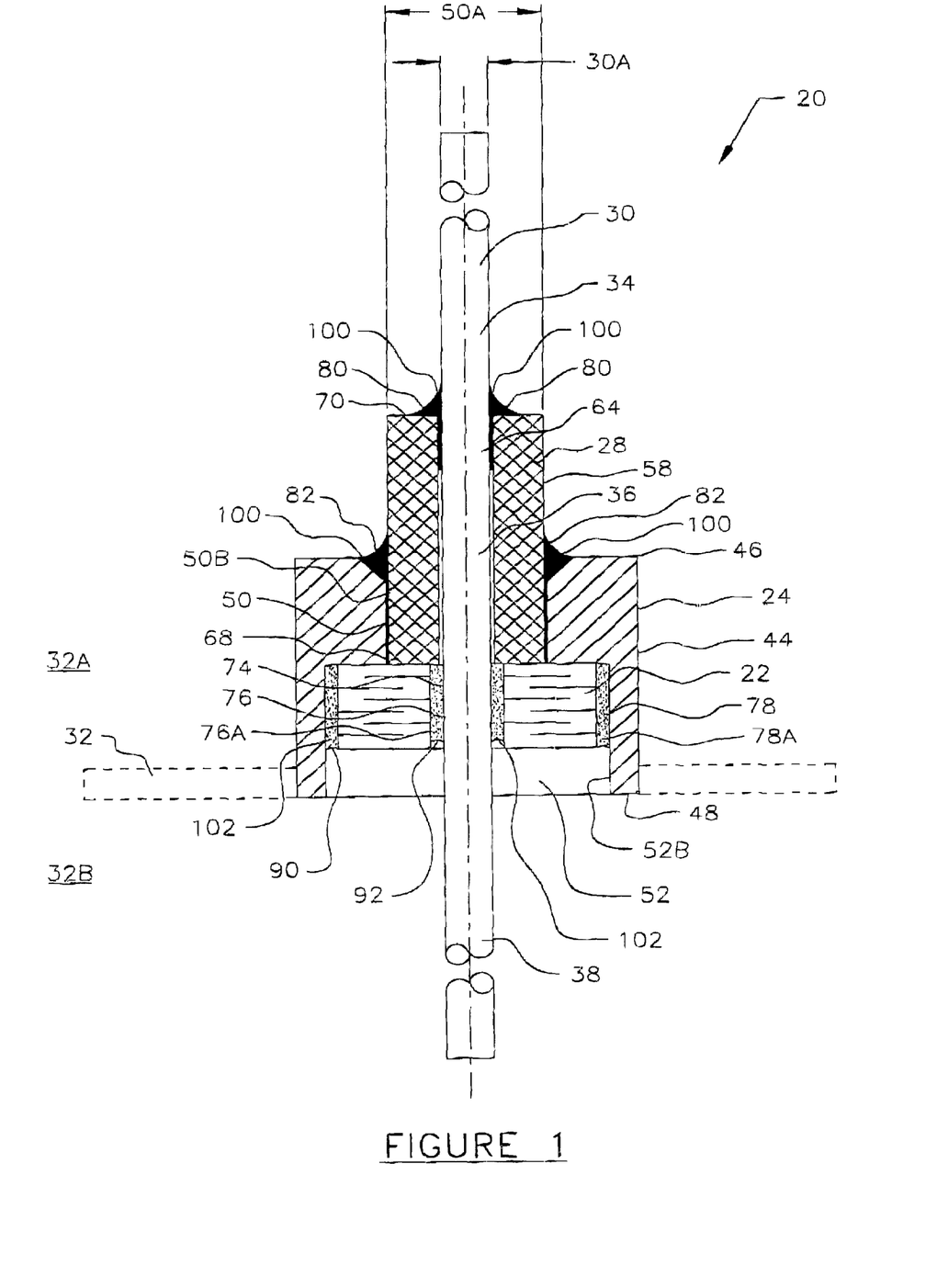
FIG. 1 shows a side elevational full cutaway view of the feedthrough device of the invention.

Turning first to FIG. 1, the invention provides for a novel filtered feedthrough device or assembly 20 (hereinafter feedthrough 20) that incorporates braze joints for installing one or more capacitors 22 in a ferrule 24 of the feedthrough 20. The constituent parts of the feedthrough 20 are first described in detail, these parts comprising the ferrule 24, the capacitor 22, an insulator 28, and a conductive lead wire or conductive pin 30 (hereinafter lead 30). Then the insulator-ferrule braze joint 82, the insulator-lead braze joint 80, the capacitor-ferrule braze joint 90 and the capacitor-lead braze joint 92 are described in detail. Ferrule 24 may be welded or otherwise joined to the housing 32 of an implantable medical device such as an implantable cardiac pacemaker or an implantable cardiac defibrillator. The feedthrough 20 is for allowing the conductive lead 30 to pass from the interior 32B of the housing 32 to the exterior 32A of the housing 32 in a nonconductive manner, i.e., electrically insulated from the housing 32 that is typically embodied as a metal such as titanium.

The lead or pin 30 comprises an external portion 34, a feedthrough portion 36, and an internal portion 38, and may be embodied as having a cylindrical shape with a diameter designated 30A. The lead 30 is constructed of a conductive material such as platinum-iridium alloys, niobium, or pure platinum so that it can carry the electrical impulses from the pulse generator (not shown) within the housing 32 to electrodes attached to the heart (not shown), in a manner well known to those skilled in the art.

The ferrule 24, also constructed of metal, is embodied as a cylindrical structure having a cylindrical exterior sidewall 44 and has an insulator end 46 and a capacitor end 48. The ferrule 24 further comprises an insulator receiving recess 50 having a diameter designated 50A in FIGS. 1 and 2, and a capacitor receiving recess 52 having a diameter designated 52A in FIG. 2. It is noted that while the figures show the insulator receiving recess 50 and the capacitor receiving recess 52 as cylindrically shaped, these recesses may be embodied in other shapes, for example rectangular shaped recesses to accommodate rectangular shaped capacitors and insulators.

Figure 2:
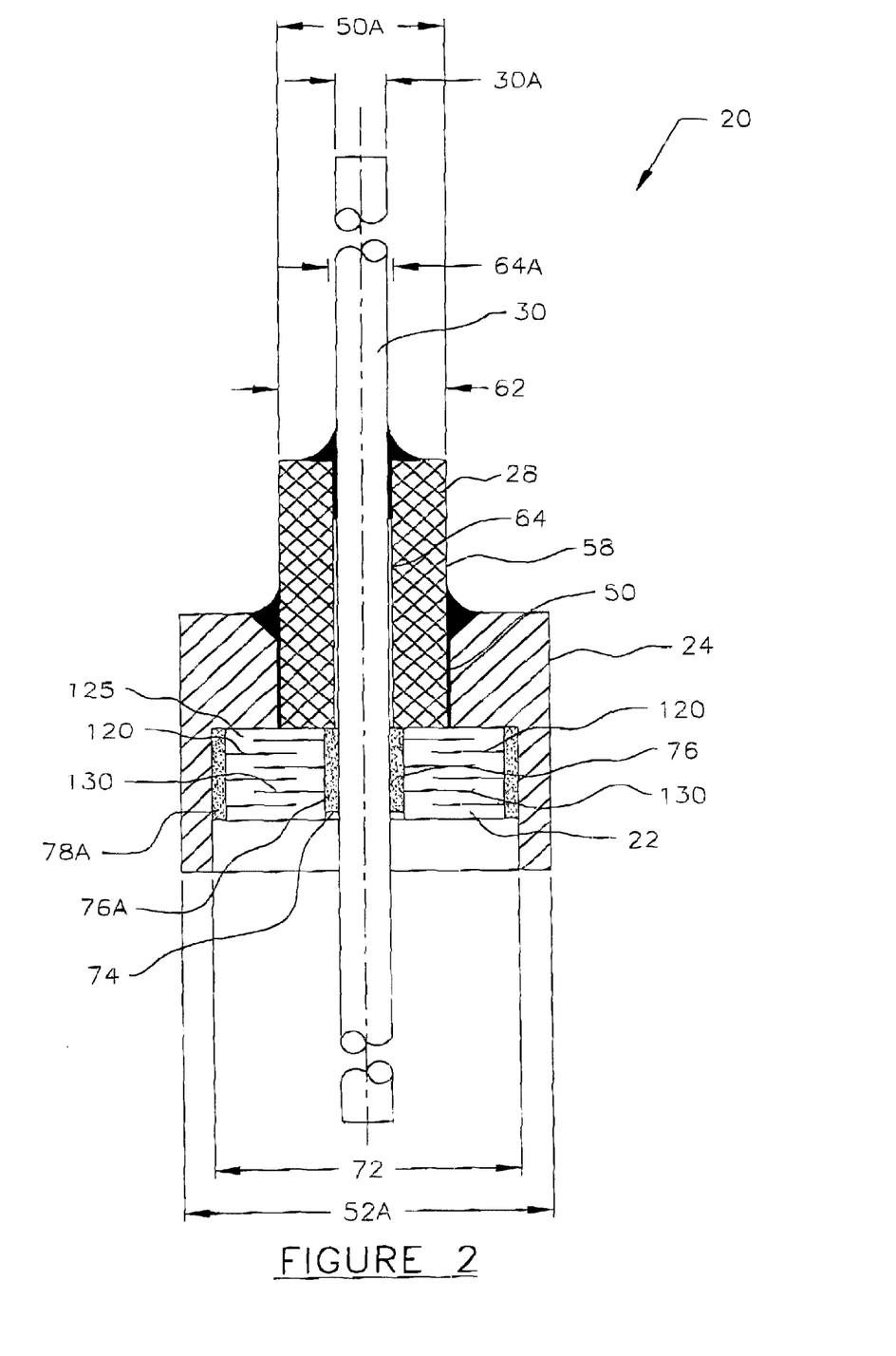
FIG. 2 shows a side elevational full cutaway view the same as FIG. 1 that further illustrates the feedthrough device of the invention.

The insulator 28 has a cylindrical exterior surface 58 and may be made of ceramics and other insulating materials well known to those of ordinary skill in the art. The insulator 28 has a diameter designated 62 in FIG. 2, and it has an insulator passageway 64 extending therethrough, as seen in FIG. 2. The insulator passageway 64 has a diameter designated 64A (FIG. 2) that is greater than the diameter of the lead designated 30A (FIG. 2), so that the lead 30 is receivable in and can pass through the insulator passageway 64.

The insulator 28 also has a ferrule end 68 and an exposed end 70. The diameter of the insulator, designated 62 in FIG. 2, is less than the diameter designated 50A of the insulator receiving recess 50 in the ferrule 24, so that the ferrule end 68 of the insulator 28 is receivable in the insulator receiving recess 50 in the ferrule 24. As will be described presently, a brazing process according to the invention using an insulator braze material 100 joins the insulator 28 to the ferrule 24 and the lead 30 to the insulator 28.

At the capacitor end 48 of the ferrule 24 is the capacitor receiving recess 52 having a diameter designated 52A in FIG. 2. The capacitor 22, may be embodied as a discoidal shaped capacitor and has a capacitor diameter designated 72 in FIG. 2. The cylindrical (discoidal) shaped capacitor 22 further defines a capacitor passageway 74 extending therethrough. The capacitor 22 may comprise first and second sets of metal plates 120, 130 separated by a dielectric 125 and be made to store charge and filter undesirable EMI as shown in FIG. 2. A capacitor 22 of this type is well known to those skilled in the art. The capacitor passageway 74 has a diameter greater than the lead 30 diameter 30A, so that the lead 30 may pass therethrough. The diameter of the capacitor 72 is such that it is less than diameter of the capacitor receiving recess 52A in FIG. 2, so that the capacitor 22 is receivable in the capacitor receiving recess 52 of the ferrule 24. It is noted that capacitor 22 may be embodied such that it is completely received in the capacitor receiving recess 52, or only partly received in the capacitor receiving recess 52, or the ferrule 24 may be embodied such that it completely or partly receives the capacitor 22 therein.

The capacitor passageway 74 has an internal surface 76 provided with a metallized internal surface layer 76A. The capacitor 22 further comprises an exterior capacitor surface 78 about its circumference that also has a metallized external surface layer indicated by reference number 78A. As described above the capacitor 22 may comprise first and second sets of metal plates 120, 130 respectively shown in FIG. 2. The second set of metal plates 130 makes contact with the metallized internal surface layer 76A, and the first set of plates 120 makes contact with the metallized external surface layer 78A of the capacitor 22. The first and second sets of plates 120,130 may be of metal and separated by layers of a dielectric material, such capacitors and configurations being well known to those to those skilled in the art. Indeed, the plates 120,130 and dielectric 125 may be made of a plurality of different materials having the requisite properties to filter undesirable EMI, such capacitors being well known to those skilled in the art.

The assembly of the feedthrough 20 will now be described followed by a description of the brazing processes. The brazing of the feedthrough 20 is actually a two step process. In the first step, the ferrule end 68 of the insulator 28 is inserted into the insulator receiving recess 50 in the ferrule 24 and brazed thereto using an insulator braze material 100. Since the insulator diameter designated 62 is less than the diameter of the insulator receiving recess designated 50A, there is room between the exterior cylindrical surface 58 of the insulator 28 and the insulator receiving recess sidewall 50B in the ferrule 24, and that allows for the smooth insertion of the insulator 28 therein. The lead 30, because it has a diameter designated 30A that is less than the diameter designated 64A (FIG. 2) of the insulator passageway 64, is fitted into and passed through the insulator passageway 64. The lead 30 is also brazed to the insulator 28 in the first step using the insulator braze material 100.

In such a configuration and as seen in FIG. 1, an insulator-lead braze joint 80 (generated in a manner described below), is formed between the insulator 28 and the lead 30. The insulator-lead braze joint 80 extends annularly about the circumference of the exposed end 70 of the insulator 28 and the lead 30, and the insulator-lead braze joint 80 contacts the lead 30 and insulator 28 joining the lead 30 and the insulator 28. Also, an insulator-ferrule braze joint 82 (generated in a manner described presently) is formed between the insulator 28 and the ferrule 24, also seen in FIG. 1. The insulator-ferrule braze joint 82 extends about the circumference of the insulator 28 at the point where the insulator 28 enters the insulator receiving recess 50 in the ferrule 24. The insulator braze material 100 used for the insulator-lead braze joint 80 and the insulator-ferrule braze joint 82 is the same.

In the second step, a capacitor braze material 102 is utilized to join the metallized external surface layer 78A of the of the capacitor 22 to the interior sidewall 52B of the capacitor receiving recess 52, and to join the metallized internal surface layer 76A of the capacitor passageway 74 to the lead 30. The second step thus forms the capacitor-ferrule braze joint 90 and the capacitor-lead braze joint 92 using the capacitor braze material 102.

Brazing (braze welding) may be employed to accomplish the brazing of the insulator-lead braze joint 80 and the insulator-ferrule braze joint 82. The technique for brazing each of these described presently. The insulator-lead braze joint 80 and the insulator-ferrule braze joint 82 may be formed by brazing techniques well known to those skilled in the art, for example by placing the insulator braze material 100 at the location where the braze joint is to be formed and then applying heat to the insulator braze material 100 at a temperature sufficient to form the joint. Then, upon cooling, the insulator-lead braze joint 80 and the insulator-ferrule braze joint 82, made of the insulator braze material 100, form a hermetic seal between the lead 30 and the insulator 28 and between the insulator 28 and the ferrule 24.

The insulator braze materials 100 used for brazing the insulator-ferrule braze joint 82 and for brazing the insulator-lead braze joint 80 comprise:

pure gold;
gold alloys comprising at least one of tin, copper, silver, palladium, indium, titanium, niobium, vanadium, nickel, molybdenum, platinum;
silver;
silver alloys containing at least one of gallium, palladium, and aluminum; and
copper silver alloys that may contain tin, indium, palladium, nickel, gallium, palladium, and titanium.

As described presently, the above described insulator braze material 100 used for the insulator-ferrule braze joint 82 and the insulator-lead braze joint 80 are different from the capacitor braze material 102 used in forming the capacitor-ferrule braze joint 90 and capacitor-lead braze joint 92, in that the capacitor braze material 102 has a lower liquidus.

The capacitor braze materials 102 that may be used for brazing the capacitor-ferrule braze joint 90 and the capacitor-lead braze joint 92 comprise:

seventy-two percent silver and twenty-eight percent copper;
copper and silver and at least one of the following elements: titanium, indium, manganese, gallium, palladium, platinum, nickel or tin, so long as they are compatible with the capacitor 22 termination materials;
silver-germanium alloys,
gold alloys,
and silver-palladium-gallium alloys so long as these materials are compatible with capacitor termination materials.

To facilitate brazing of the capacitor-ferrule braze joint 90 and the capacitor-lead braze joint 92 a thread-type preform (not shown in the figures) of capacitor braze material 102 may be threaded onto the lead 30, and an annular shaped capacitor preform (not shown in the figures), of capacitor braze material 102, having a diameter substantially the same as the capacitor diameter designated 72 may positioned about the exterior capacitor surface 78. The capacitor braze material 102 for the thread-type preform and capacitor preform is selected from the above described brazes for the capacitor-ferrule braze joint 90 and capacitor-lead braze joint 92. Upon brazing, the annular shaped capacitor preform melts and the capacitor braze material 102 seeps into or is drawn into the space between the exterior capacitor surface 78 and the interior sidewall 52B of the ferrule 24, and the thread-type preform melts and seeps into the space between the lead 30 and metallized internal surface layer 76A of the capacitor passageway 74.

Brazing Process

The following example is an embodiment of the brazing process that is itself a two step procedure, wherein the first step provides for forming the ferrule-insulator braze joint 82 and the insulator-lead braze joint 80 (hereinafter braze joints 80,82), this brazing being accomplished at a first temperature. Braze joints 80,82 are brazed first using the above described insulator braze materials 100 for the insulator-ferrule braze joint 82 and the insulator-lead braze joint 80. After brazing, the insulator 28 is securely joined to the ferrule 24 and the lead 30 is securely joined to the insulator 28.

The next step for forming the feedthrough 20 calls for the brazing of the capacitor 22 in the ferrule 24 using the capacitor braze materials 102, these braze materials having different properties, such as lower eutectic melting temperatures, than the insulator braze materials 100 used in the first step. The capacitor receiving recess 52 has positioned adjacent thereto an annular shaped capacitor preform (not shown in the figures) made of capacitor braze material 102. The annular shaped braze preform having a diameter such that is substantially the same as the diameter of the capacitor receiving recess 52A. The portion of the lead 30 received in the capacitor passageway 74 is wrapped in a thread-type preform (not shown in the figures) made of capacitor braze material 102. The capacitor braze material 102 is initially seated above the capacitor-ferrule braze joint 90 and capacitor-lead braze joint 92, and upon brazing, capacitor braze material 102 flows into the space between the metallized external surface layer 78A of the of the capacitor 22 and the interior sidewall 52B of the capacitor receiving recess 52, thus forming the capacitor-ferrule braze joint 90. The melted capacitor braze material 102 also flows between the metallized internal surface layer 76A of the capacitor passageway 74 and the lead 30, thus forming the capacitor-lead braze joint 92. The flow of the melted capacitor braze material 102 is due to capillary and wetting forces.

The second step of brazing calls for the brazing of the capacitor-ferrule braze joint 90 and capacitor-lead braze joint 92, and this brazing occurs at a second temperature lower than the brazing temperatures of the first step, wherein the insulator-ferrule braze joint 82 and insulator lead braze joint 80 were formed. This is because the capacitor braze material 102 has a lower melting or liquidus temperature than that of the insulator braze material 100. One of the advantages with the brazing of the second step being done at a lower temperature than the brazing in the first step is that the lower temperature does not affect the hermetic seal formed by the previously brazed insulator-ferrule braze joint 82 and insulator lead braze joint 80.

An example of the two step brazing process of the present invention follows. First, the insulator-ferrule braze joint 82 and the insulator-lead braze joint 80 are formed by using, for example pure gold for the insulator braze material 100, that melts at 1063 degrees centigrade. The method of brazing known to those skilled in the art.

Then, the capacitor-ferrule braze joint 90 and capacitor-lead braze joint 92 are formed using a 72% silver 28% copper capacitor braze material 102 having a eutectic melting temperature of 780 degrees centigrade. The braze preforms made of the capacitor braze material 102 for the capacitor-ferrule braze joint 90 and for the capacitor-lead braze joint 92 are installed in the feedthrough 20 as previously described and the feedthrough 20 assembly is heated in a vacuum furnace (not shown) to a temperature exceeding the 780 degree centigrade eutectic melting point of the seventy-two percent silver and twenty-eight percent copper capacitor braze material 102. Upon melting, the capacitor braze material 102 wets the interior sidewall 52B of the capacitor receiving recess 52 and the metallized external surface layer 78A of the exterior capacitor surface 78 and flows therebetween. The capacitor braze material 102 also wets the lead 30 and the metallized internal surface layer 76A of the internal surface 76 of the capacitor passageway 74 and flows therebetween. After brazing, the feedthrough 20 is then left to cool, and when cooled, the capacitor braze material 102 cools and solidifies forming a robust metallurgical and electrical connection, thus joining the capacitor 22 and the lead 30 and joining the capacitor 22 and the ferrule 24.

After the brazing process, the first set of capacitor plates 120 is conductively coupled to the ferrule 24 and the second set of plates 130 is conductively coupled to the lead 30. Also, after brazing, the lead 30 passes through the feedthrough 20 in a nonconductive manner. Thus, the solidified capacitor braze material 102 forms a robust mechanical and electrical connection directly from the exterior capacitor surface 78 of the capacitor 22 to the ferrule 24 and from the internal surface 76 of the capacitor passageway 74 of the capacitor 22 to the lead or pin 30. Further, after brazing, the feedthrough 20 is hermetically sealed. The feedthough 20 may then be joined to the housing 32 after brazing is complete.

Thus the present invention provides a filter capacitor feedthrough assembly 20 including an all braze arrangement wherein capacitor braze material 102 joins the capacitor 22 to the feedthrough pin or lead 30 and to the ferrule 24, and wherein insulator braze material 100 joins the insulator 28 to the pin or lead 30 and to the ferrule 24. The braze arrangement and method according to the invention has a number of important distinctions and advantages over prior art assemblies and methods utilizing soldered joints. One difference is the temperature levels at which the respective operations are performed and to which the resulting joints can be exposed subsequently before they fail. Brazing may be defined as a group of joining processes which produces a coalescence of materials by heating them to a suitable temperature and by using a filler metal having a liquidus above 448.9 degrees centigrade and below the solidus of the base metal. Soldering may be defined as a group of joining processes which produces coalescence of materials by heating them to a suitable temperature and using a filler metal having a liquidus not exceeding 448.9 degrees centigrade and below the solidus of the base metal.

Another distinction involves how the bond is established. Adhesion is the primary mechanism in soldering, but in brazing, alloying and diffusion are the principal means of establishing the bond. The temperature to which a brazed joint can be exposed after formation is higher than the temperature to which a soldered joint can be exposed, because the solder can remelt at a lower temperature, threatening the integrity of the joint.

Furthermore, in soldering only mechanical bonded joints are formed, whereas in brazing a metallurgical joint is formed. Moreover, in soldering fluxes are typically required, whereas in brazing the use of flux is optional. Finally, in soldering the heat is supplied by a soldering iron, ultrasonic devices, resistance, ovens, etc, whereas in brazing the heat is supplied by a furnace, chemical reaction, induction torch, infrared, etc.

In the process of the invention, the brazing of the capacitor 22 is conducted at a temperature above 780 degrees centigrade, well above the minimum temperature for brazing. The brazing operation is performed in a brazing furnace, whereas the soldering operation is performed in a lower temperature oven. A flux is not used in the brazing process of the invention. This is an advantage, because it eliminates a processing step and avoids a cleaning operation and possible contamination of the implantable medical device by residual flux material.

The fact that the brazed joint can be exposed to a higher temperature than can a soldered joint is another important advantage and distinction of brazing. The feedthrough of the invention may be ultimately welded to the case of an implantable medical device. A soldered joint may be exposed to a temperature high enough to melt the solder during the welding process, potentially causing the reflow of the solder and even freeing part of the solder from the base metal. If the latter were to happen, a "solder ball" could form which might fall from the feedthrough into the pacemaker or defibrillator, potentially causing a short circuit within the device if it touches any electronic components.

Figure 3:
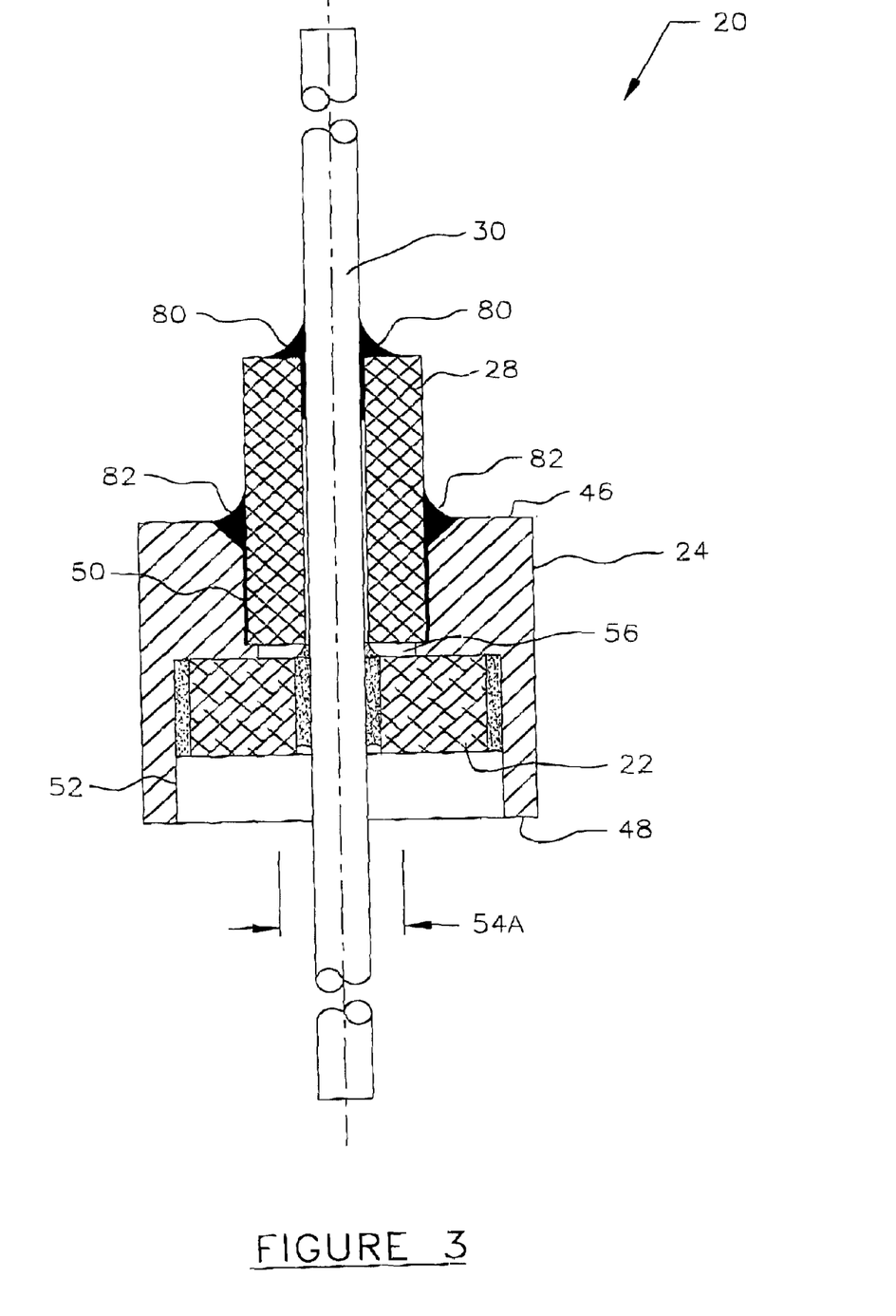
FIG. 3 shows a side elevational full cutaway view of an alternative embodiment of the feedthrough device of the invention.

In a second embodiment of the present invention, seen in FIG. 3, the ferrule 24 is provided with an internal lip 56 positioned between the insulator receiving recess 50 and the capacitor recess 52. In this embodiment the intermediate recess 54 has a diameter designated 54A that is less than the diameters of the insulator receiving recess 50 and capacitor receiving recess 52, and the insulator 28 does not contact the capacitor 22 as is the case in the first embodiment of the present invention. During the two step brazing process, the braze materials may be selected from the above described lists of braze materials and accomplished in the manner described with respect to the first embodiment.

Figure 4:
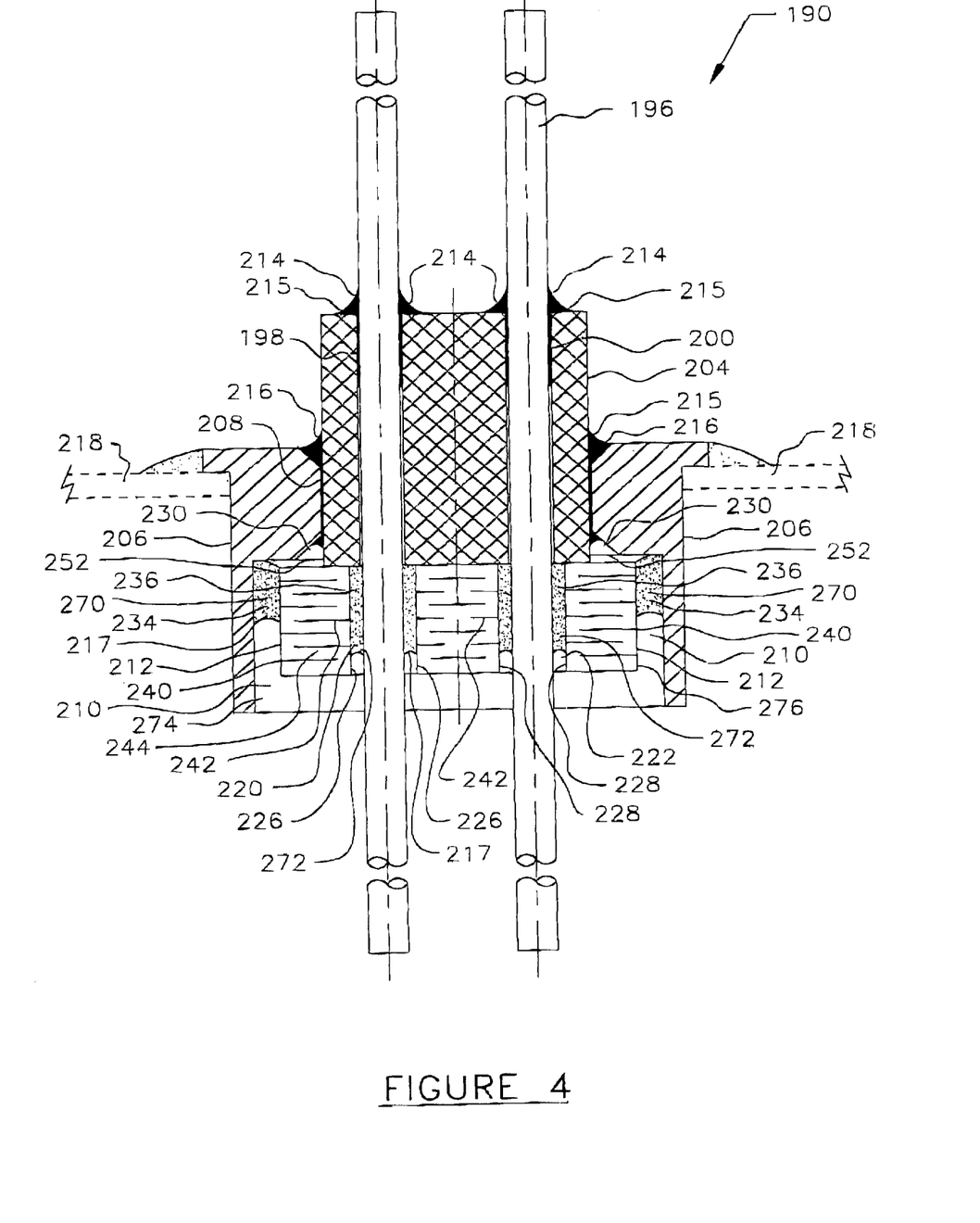
FIG. 4 shows a side elevational full cutaway view of an alternative embodiment of the feedthrough device comprising a plurality of leads.

In a third embodiment of the invention, shown in FIG. 4, the feedthrough 190 is provided with a plurality of conductive leads 194,196 that pass through a plurality of lead passageways 198, 200 defined in the insulator 204. The insulator 204 is received in the insulator receiving recess 208 in the ferrule 206. The capacitor 212 is received in the capacitor receiving recess 210 in the ferrule 206. The insulator 204 protrudes a distance into the capacitor recess 210 and contacts the capacitor 212. In a manner substantially the same as the brazing processes and procedures fully described above for the first embodiment of the invention, the insulator 204 is brazed to the plurality of leads 194,196 and to the ferrule 206 with an insulator braze material 215, and the capacitor 212 is brazed to the ferrule 206 and to the plurality of leads 194,196 with a capacitor braze material 217. The braze joints between leads 194,196 and the insulator 204 and between the insulator 204 and the ferrule 206 are indicated by reference numbers 214 and 216 respectively and are made of the insulator braze material 215. The insulator braze material 215 and the capacitor braze material 217 may be embodied as the same insulator braze materials 100 and capacitor braze materials 102 as described in the first embodiment of the present invention.

The feedthrough 200 may be mounted on a housing 218 that may be an implantable medical device such as the housing of a pacemaker or defibrillator (not shown). A joint 219 is formed where the feedthrough 200 is mounted to the housing 218, the manner of mounting and forming joint 219 known to those skilled in the art.

The same two step brazing process as described in the first embodiment is employed to braze the feedthrough of the third embodiment.

In particular, in the first step, the insulator braze materials 215 for the insulator-lead braze joint 214 and the insulator-ferule braze joint 216 may comprise:

pure gold;

gold alloys comprising at least one of tin, copper, silver, palladium, indium, titanium, niobium, vanadium, nickel, molybdenum, platinum;

silver;
silver alloys containing at least one of gallium, palladium, and aluminum; and
copper silver alloys that may contain tin, indium, palladium, nickel, gallium, palladium, and titanium.

The second step involves brazing the capacitor 212 to the ferrule 206 and to the plurality of leads 194, 196. The capacitor 212 may be discoidal in shape, and may be embodied to have a pair of capacitor passageways 220 and 222 to receive leads 194 and 196 respectively. A metallized external surface layer 224 is located about the circumference of the capacitor 212. The capacitor passageways 220 and 222 have metallized internal surface layers 226 and 228 respectively. An annular braze preform (not shown) made of capacitor braze material 217 is positioned about the capacitor 212 and the thread type braze preforms (not shown) made of capacitor braze material 217 are threaded to the leads 194 and 196, respectfully. The braze preforms made of capacitor braze material 217 are used to form the capacitor-ferrule braze joint 270 and the capacitor-lead braze joint 272 respectively, and the capacitor braze material 217 may be embodied to comprise the following:
seventy-two percent silver and twenty-eight percent copper;
copper and silver and at least one of the following elements: titanium, indium, gallium, palladium, platinum, nickel or tin, so long as they are compatible with the capacitor 22 termination materials;
silver-germanium alloys,
gold alloys,
and silver-palladium-gallium alloys so long as these materials are compatible with capacitor termination materials.

As with the first embodiment, in the third embodiment the ferrule-capacitor braze joint 270 and capacitor-lead braze joints 272 may use a capacitor braze material 217 comprising seventy-two percent silver and twenty-eight percent copper. The feedthrough 190 may then be assembled and heated in a vacuum furnace (not shown) to a temperature exceeding the 780 degree Centigrade eutectic melting point of the seventy-two percent silver and twenty-eight percent copper braze. Upon melting, the braze material wets the interior sidewall 274 of the capacitor receiving recess 210 and the metallized external surface layer of the capacitor 276. After brazing the feedthrough 190 is then left to cool, the ferrule-capacitor braze joint 270 and capacitor-lead braze joints 272 form a robust metallurgical and electrical connection, thus joining the capacitor 212 to the ferrule 206 and joining the leads 194, 196 to the capacitor.

The capacitor itself may have first and second sets of plates 240, 242 respectively, separated by a dielectric material 244. The first set of plates 240 contacts the ferrule 206 through the capacitor-ferrule braze joint 270 and the second set of plates 242 contacts the leads 194,196 through the capacitor-lead braze joints 272.

After the brazing process, the first set of capacitor plates 240 is conductively coupled to the ferrule 206 and the second set of plates 242 is conductively coupled to the leads 194,196. Thus, the solidified braze forms a robust mechanical and electrical connection directly from the capacitor 212 to the ferrule 206 and from the capacitor 212 to the leads 194,196.

Also, the ferrule 206 has a chamfered annular internal surface 230 that defines a gap space 252 when the insulator 204 and capacitor 212 are positioned in the ferrule 206, as seen in FIG. 4. This gap space 232 may fill partly with melted insulator braze material 215 during the brazing process. Thus, the two step brazing process fully described in the first embodiment may be employed in the third embodiment of the present invention.

Thus, the present invention provides a new way to install capacitor filters in feedthrough devices. Although several embodiments of the invention have been described herein, various modifications may be made without departing from the scope of the invention. All of these alternative embodiments are intended to be within the scope and spirit of the appended claims.

What is claimed:

1. A feedthrough comprising:
   a lead;
   a ferrule defining a capacitor receiving recess and the ferrule also defining an insulator receiving recess;
   a capacitor disposed in the capacitor receiving recess, the capacitor defining a capacitor passageway for the lead to pass;
   an insulator disposed in the insulator receiving recess, the insulator defining an insulator passageway for the lead to pass through;
   an insulator braze material for forming an insulator-ferrule braze joint and for forming an insulator-lead braze joint; and
   a capacitor braze material for forming a capacitor-ferrule braze joint and for forming a capacitor-lead braze joint, wherein the insulator braze material is different than the capacitor braze material wherein and the insulator-ferrule braze joint and the insulator-lead braze joint are brazed before the capacitor-ferrule braze joint the capacitor-lead braze joint are brazed.

2. The feedthrough of claim 1 wherein the capacitor comprises a first set of plates and comprises a second set of plates, and wherein the first set of plates is conductively coupled to the ferrule by the capacitor braze material and the second set of plates is conductively coupled to the lead by way of the capacitor braze material, the first set of plates and the second set of plates for filtering electromagnetic interference, and wherein the capacitor braze material is selected from the group consisting of:
   seventy-two percent silver and twenty-eight percent copper;
   copper and silver and one of the following elements selected from the group consisting of: titanium, indium, gallium, palladium, platinum, nickel, and tin;
   silver-germanium alloys;
   gold alloys;
   silver-palladium-gallium alloys; and
   copper and silver alloys comprising at least one of the elements selected from the group consisting of titanium, indium, gallium, palladium, platinum, nickel and tin.

3. The feedthrough of claim 1 wherein the capacitor braze material used for the capacitor-ferrule braze joint and for the capacitor-lead braze joint comprises seventy-two percent silver and twenty-eight percent copper.

4. The feedthrough of claim 1 wherein the capacitor braze material used for the capacitor-ferrule braze joint and for the capacitor-lead braze joint comprises copper and silver one of the following elements selected from the group consisting of: titanium, indium, gallium, palladium, platinum, nickel, and tin.

5. The feedthrough of claim 1 wherein the capacitor braze material for the capacitor-ferrule braze joint and the capacitor-lead braze joint is selected from the group consisting of:
   silver-germanium alloys;
   gold alloys;

silver-palladium-gallium alloys; and copper and silver alloys comprising at least one of the elements selected from the group consisting of titanium, indium, gallium, palladium, platinum, nickel and tin.

6. The feedthrough of claim 1 wherein the insulator braze material for the insulator-ferrule braze joint and the insulator-lead braze joint comprises gold.

7. The feedthrough of claim 1 wherein the insulator braze material for the insulator-ferrule braze joint and the insulator lead braze joint is selected from the group consisting of:

gold alloys comprising at least one of the following selected from the group consisting of: tin, copper, silver, palladium, indium, titanium, niobium, vanadium, nickel, molybdenum, platinum;

silver;

silver alloys comprising at least one of the following selected from the group consisting of:

gallium, palladium, and aluminum;

copper silver alloys; and copper silver alloys comprising at least one of the following selected from the group consisting of: tin, indium, palladium, nickel, gallium, palladium, and titanium.

8. The feedthrough of claim 2 wherein the ferrule further comprises an interior sidewall for defining the capacitor receiving recess, and the capacitor comprises an exterior capacitor surface provided with a metallized external surface layer, and the capacitor further comprises an internal surface about the capacitor passageway provided with a metallized internal surface layer, and wherein the capacitor braze material upon melting flows between the interior sidewall of the ferrule and the metallized external surface layer of the capacitor and flows between the metallized internal surface layer of the capacitor passageway and the lead.

9. The feedthrough of claim 8 further comprising a thread-type preform comprising capacitor braze material that is wrapped about the lead so that during brazing the thread type preform melts and flows between the lead and the metallized internal surface layer of the capacitor passageway, and the external surface of the capacitor has positioned proximate thereto an annular shaped capacitor preform of capacitor braze material so that during brazing the annular shaped capacitor braze preform melts flows between the interior sidewall of the ferrule and the metallized external surface layer of the capacitor passageway and the lead.

10. The feedthrough of claim 1 wherein the insulator-ferrule braze joint and the insulator-lead braze joint is brazed at first temperature and the capacitor-ferrule braze joint and capacitor-lead braze is braze at a second temperature, the second temperature being less than the first temperature.

11. The feedthrough of claim 10 wherein a thread-type preform wrapped around the lead prior to brazing and the annular shaped capacitor preform for positioning proximate to the exterior capacitor surface comprise seventy-two percent silver and twenty-eight percent copper.

12. The feedthrough of claim 1 wherein the insulator is positioned in the insulator receiving recess and the capacitor is positioned in the capacitor receiving recess such that they contact one another and the lead passes through the ferrule in a nonconductive manner.

13. The feedthough of claim 12 wherein the ferrule is joined to an implantable medical device comprising a housing having an interior, such that the lead passes from the interior of the housing to a location external to the housing by way of the feedthrough in a nonconductive manner.

14. A feedthrough comprising;

a lead a ferrule defining an insulator receiving recess and an insulator disposed in the insulator receiving recess, the insulator defining a passageway for the lead to pass therethrough, the insulator brazed to the ferrule brazed to the lead with an insulator braze material, the ferrule further defining a capacitor receiving recess into which a capacitor is disposed, the capacitor comprising capacitor exterior surface and defining a capacitor passageway for the lead to pass therethrough, and a thread-type preform threaded about the lead at the location where the lead is proximate the capacitor passageway, and an annular capacitor preform positioned adjacent to the capacitor exterior surface, wherein the thread-type preform and the capacitor preform are made of a capacitor braze material and wherein the insulator braze material has a higher melting temperature than the capacitor braze material.

15. The feedthrough of claim 14 wherein the capacitor braze material from which the thread-type preform and the annular capacitor preform are made comprising seventy-two percent silver and twenty-eight percent copper.

16. The feedthrough of claim 14 wherein the thread-type preform and the annular capacitor preform are made from a capacitor braze material comprising copper and silver at least one of the following materials selected from the group consisting of: titanium, indium, gallium, palladium, platinum, nickel, and tin.

17. The feedthrough of claim 14 wherein the thread-type preform and the capacitor preform are made from a capacitor braze material selected from the group consisting of: silver-germanium alloys, gold alloys, and silver-palladium-gallium alloys.

18. The feedthrough of claim 14 where the capacitor braze material is selected from the group consisting of:

seventy-two percent silver and twenty-eight percent copper;

copper and silver and at least one of the following selected from the group:

titanium, indium, gallium, palladium, platinum, nickel, and tin; and silver-germanium alloys, gold alloys, and silver-palladium-gallium alloys.

19. The feedthrough of claim 14 wherein the insulator and the ferrule form an insulator-ferrule braze joint and the insulator and the lead form an insulator-lead braze joint, and the capacitor and the ferrule form a capacitor-ferrule braze joint and the capacitor and the lead form a capacitor-lead braze joint, and wherein the insulator braze material is used for brazing the insulator-ferrule braze joint and the insulator-lead braze joint has a higher melting temperature than the capacitor braze material used for forming the capacitor-ferrule braze joint and the capacitor-lead braze joint, the insulator-ferrule braze joint and the insulator-lead braze joint are formed before the capacitor-ferrule braze joint and the capacitor-lead braze joint are formed.

20. A feedthrough comprising:

a plurality of leads;

a ferrule defining a capacitor receiving recess and the ferrule also defining an insulator receiving recess;

a capacitor disposed in the capacitor receiving recess, the capacitor defining a plurality of capacitor passageway for the plurality of leads to pass;

an insulator disposed in the insulator receiving recess, the insulator defining a plurality of insulator passageways for the lead to pass through;

an insulator braze material for forming an insulator-ferrule braze joint and for forming an insulator-lead braze joint; and a capacitor braze material for forming a capacitor-ferrule braze joint and for forming a capacitor-lead braze joint, wherein the insulator braze material is different than the capacitor braze material wherein and the insulator-ferrule braze joint and the insulator-lead braze joint are brazed before the capacitor-ferrule braze joint the capacitor-lead braze joint are brazed.

* * * * *